United States Patent [19]

Pasula

[11] Patent Number: 5,147,785
[45] Date of Patent: * Sep. 15, 1992

[54] METHOD AND APPARATUS FOR MEASURING THE DEGREE OF REACTION BETWEEN A FOREIGN ENTITY AND WHITE BLOOD CELLS

[75] Inventor: Mark J. Pasula, Miami, Fla.

[73] Assignee: Amtl Corporation, Hollywood, Fla.

[*] Notice: The portion of the term of this patent subsequent to Sep. 30, 2003 has been disclaimed.

[21] Appl. No.: 363,854

[22] Filed: Jun. 9, 1989

Related U.S. Application Data

[63] Continuation of Ser. No. 902,313, Aug. 28, 1986, abandoned, which is a continuation-in-part of Ser. No. 547,767, Nov. 1, 1983, Pat. No. 4,614,722.

[51] Int. Cl.$^5$ ............................................. G01N 33/53
[52] U.S. Cl. ................................... 435/7.24; 436/501; 436/513; 436/63; 424/91; 435/7.1; 435/7.25
[58] Field of Search ................. 436/501, 513, 519, 63; 424/91; 324/71.1, 71.2; 377/10, 11, 12; 435/7, 7.1, 7.24, 7.25

[56] References Cited

U.S. PATENT DOCUMENTS

| 4,614,722 | 9/1986 | Pasula | 436/501 |
| 4,743,540 | 5/1988 | Ralph et al. | 435/6 |

*Primary Examiner*—David L. Lacey
*Assistant Examiner*—Laurie A. Scheiner
*Attorney, Agent, or Firm*—Roger S. Thompson

[57] ABSTRACT

Briefly stated, the invention is directed to a method for the diagnosis of a malady in a subject by the observing of a degree of reaction between the leukocytes in the subject's blood with a foreign entity having a predetermined relationship with the malady being diagnosed.

19 Claims, 2 Drawing Sheets

METHOD AND APPARATUS FOR MEASURING THE DEGREE OF REACTION BETWEEN A FOREIGN ENTITY AND WHITE BLOOD CELLS

CROSS-REFERENCE TO RELATED APPLICATION

This application is a continuation application of Ser. No. 06/902,313 filed Aug. 28, 1986, now abandoned, which is a continuation-in-part application of my co-pending application Ser. No. 547,767, filed Nov. 1, 1983, Issued as U.S. Pat. No. 4,614,722, on Nov. 1, 1986.

BACKGROUND OF THE INVENTION

This invention relates to the field of cellular immune reactions; and, more particularly, to a method and apparatus for the direct and/or indirect determination of the degree of reaction (if any) between a foreign entity and a subject's white blood cells, for diagnosing a malady of the subject.

Diagnosing maladies is perhaps the single most important aspect of medicine. The key to diagnosing a malady is based on an understanding of the malady's cause.

Many illnesses and afflictions (i.e. maladies other than illnesses, such as an allergy or cancer) are caused by an individual's coming into contact with foreign entities, such as environmental chemicals, including known or possible carcinogens, other toxins or micro-organisms, including viruses and bacteria.

Every day, the human body is exposed to many types of foreign entities, and when so exposed, the body may ingest some foreign entities, by eating or breathing them in, or perhaps merely by touch. Once a foreign entity is ingested, the body identifies it either as being neutral, in which case the body does not react in any extraordinary fashion, or identifies it as being potentially harmful, in which case the body acts to defend itself.

If the foreign entity is in fact harmful, such as a carcinogen or a virus, it will cause certain ill effects to the individual, such as disease. However, even if the foreign entity is benign, and might not cause any untoward effects by itself, the reaction of the body to its identification as being harmful may have its own set of ill effects, such as an allergic reaction.

The body's defenses, primarily the immune system, and the manner in which they act to defend the body, have been greatly studied. In broad terms, the white blood cells (leukocytes) in an individual's blood act as the first line of defense against foreign entities classified as harmful. Once a foreign entity is identified as being harmful, besides the natural (innate) immune response, the body may produce specific antibodies which combine with the foreign entity and, in conjunction with the leukocytes, destroy the invading foreign entity.

I have observed three different steps in the response of the leukocytes to a foreign entity identified as harmful, after the antibodies and leukocytes combine.

First, the leukocyte increases in volume, to surround and enclose the foreign entity. This reaction is similar or identical to a phagocytosis reaction, in which a cell ingests a particle, Bellanti, J. A., Immunology III, W. B. Saunders Co. (1985), p. 16.

Second, after the foreign entity is enclosed by the leukocyte, the volume of the leukocyte decreases in a so-called complement reaction, i.e. the leukocyte develops a small defect in its cell membrane, and begins to extrude a portion of its cellular material, Bryant, N. J., Immunohematology, W. B. Saunders Co. (1982), pp. 54-55.

Finally, the leukocyte releases all of its cellular material, and breaks up its outer membranes. This reaction is similar to the degranulation of basophiles noticed in the presence of IgE mediated reactions, Bellanti, supra., p. 252.

Many theories exist as to the precise mechanism behind the operation of the immune system, i.e. how leukocytes recognize and define harmful foreign entities, and how antibodies are produced, etc. No currently known theory, however, explains all aspects of the body's defensive reactions. In addition, no currently known theory is generally accepted as the sole basis for explaining the reactions.

This lack of an understanding of the immune system response has hampered efforts to devise a uniform and comprehensive diagnostic tool or method for the diagnosis of a wide spectrum of maladies. Since a comprehensive understanding of the mechanics of the immune response is lacking, there is no comprehensive understanding of how maladies may be recognized at an early stage.

Currently, diagnosis of a malady is more or less by a look-up method. A subject approaches a doctor and relates his symptoms. The doctor then matches those symptoms with the symptoms of known maladies, and attempts to cull a short list of possible causes from all of the conceivable causes. Based on this list, the doctor will perform tests to isolate the cause of the malady. If there is no positive test result, then a new series of tests will be performed, and this procedure continues until a positive result is attained. This may take a great deal of time and expense, and some of the tests performed may be discomforting or even painful for the subject.

This procedure is necessary because most tests are directed to specific symptoms of an illness. For example, an illness which affects kidney function may be indicated by an increased level of urea in the subject's bodily fluids. The test, then, for that kidney ailment, would be to check the level of urea in the subject's bodily fluids. Such tests do not identify the malady per se, but rather measure an expected bodily response to the malady's presence.

The look-up method has many drawbacks, however. First, it depends upon the subject's ability to recognize symptoms. If the subject has not started to feel the effects of the malady, then he may not know enough to tell the doctor of a minor symptom which would indicate a serious malady. It is for this reason that a wide battery of tests is often prescribed for a new subject, to ascertain to the extent possible what may be ailing that subject.

These tests may be time-consuming, expensive and even painful. Additionally, if the right tests are not called for, someone may be diagnosed as being in good health, but in fact have a massive tumor (for example) which has not yet begun to cause any visible symptoms. If a subject is suffering from more than one malady, the various symptoms may also mask or disguise each other, leading to a false diagnosis.

A different problem arises if two maladies have similar symptoms. A diagnosis based on symptoms may be unable to discern two completely different maladies having similar symptoms.

Furthermore, the subjectivity of an individual as to the experiencing or relating of certain symptoms may also come into play. For example, a slight headache may not cause an individual any great concern, but may in fact indicate a brain tumor.

An incorrect and possibly fatal diagnosis is always a serious concern to doctors, and there is a serious need for an objective test which may be used to diagnose a variety of maladies, without the possibility of masking or disguising of symptoms, and which may be performed effectively, relatively inexpensively, objectively, and quickly.

Further complicating this situation is the possibility that a particular malady may not cause any noticeable symptoms until it has become quite serious. Thus, the afflicted individual may not know enough to have tests performed.

The test described in my above-referenced Patent assists in the diagnosis of allergies by a simple blood test. That Patent, however, does not disclose any applicability of the test disclosed therein beyond allergies.

Furthermore, prior tests are not useful in diagnosing maladies for which there are no antibodies produced by the subject. If the introduction of the foreign entity to the body does not result in the production of antibodies specific to the foreign entity, then the body will not react to attack it and no reaction will take place. This is the case, for example, with respect to carcinogens. Since the body may not produce any natural antibodies specific to the carcinogen, the body may not act to attack it. Thus, a cancer caused by the carcinogen is free to develop unfettered, until it is of a size sufficient to be detected by other conventional means, such as by palpation or X-ray. No early detection is possible, however, until symptoms are evident. In many instances, the onset of symptoms means imminent death.

There is thus a need for an objective test which may be used to diagnose a wider variety of maladies, and which may be used to diagnose maladies caused by the ingestion of foreign entities for which no antibodies are produced by the subject. There is also a need for a method of diagnosis in which maladies may be diagnosed at a stage before the onset of externally observable symptoms.

OBJECTS AND SUMMARY OF THE INVENTION

It is thus an object of the invention to provide a method and an apparatus for the objective determination of the degree of reaction between a foreign entity and the leukocytes of a subject.

It is a further object of the invention to provide such an improved method and apparatus where accuracy and reliability will not depend upon the subjective interpretation of symptoms by a subject or his physician.

It is another object of the invention to provide a comprehensive testing method and apparatus which may be used for the diagnosis of a wide variety of maladies, without the need for a multiplicity of tests and procedures.

It is a further object of the invention to provide a method of diagnosis which is capable of diagnosing maladies caused by foreign entities for which the body of a subject produces no antibodies.

In accordance with these and other objects of the invention there is provided a method for diagnosing the presence or absence of a malady in a subject, said method comprising the steps of: counting a number of leukocytes in a first blood sample drawn from said subject; mixing a substance having a predetermined relationship with said malady with a second blood sample drawn from said subject to form a mixture, and thereby allow leukocytes of said second blood sample to react with said substance; counting a number of unreacted and reacted leukocytes in said mixture; and comparing said number of said leukocytes counted in said first blood sample with said number of unreacted and reacted leukocytes counted in said mixture, to determine if said leukocytes in said second blood sample reacted with said substance, thereby diagnosing the presence or absence of said malady in said subject.

In accordance with a preferred embodiment of the invention, there is further provided a method for diagnosing the presence or absence of a malady in a subject having blood, said method comprising the steps of: separating a sample of said blood of said subject into a control sample and at least one test sample, each of said control sample and said at least one test sample having approximately equal distributions of leukocytes therein; lysing a portion of any red blood cells in said control sample; counting a number of leukocytes in said control sample; mixing a substance having a predetermined relationship with said malady with said at least one test sample to form a mixture, and thereby allow said leukocytes present in said at least one test sample to react with said substance, and form reacted leukocytes in said mixture if said subject suffers from said malady; lysing a portion of any red blood cells in said mixture; lysing a portion of said reacted leukocytes in said mixture; counting a number of unreacted and reacted leukocytes in said mixture; comparing said number of unreacted and reacted leukocytes in said mixture with said number of leukocytes in said control sample, to determine if at least a portion of said leukocytes in said second sample reacted with said substance, thereby indicating the presence or absence of said malady in said subject.

In accordance with a second preferred embodiment of the invention, there is further provided a method for diagnosing the presence or absence of a malady in a subject, said method comprising the steps of: sizing a number of leukocytes in a first blood sample drawn from said subject; mixing a substance having a predetermined relationship with said malady with a second blood sample drawn from said subject to form a mixture, and thereby allow leukocytes present in said second blood sample to react with said second blood sample; sizing a number of unreacted and reacted leukocytes in said mixture; and comparing said sized leukocytes of said first blood sample with said sized unreacted and reacted leukocytes of said mixture, to determine thereby if at least a portion of said leukocytes in said second blood sample reacted with said substance, whereby the presence of said malady in said subject is indicated by a significant difference therebetween.

In accordance with a third preferred embodiment of the invention, there is further provided a method for diagnosing the presence or absence of a malady in a subject, said method comprising the steps of: separating a blood sample drawn from said subject into a control sample and at least one test sample, each of said control sample and said at least one test sample having approximately equal distributions of leukocytes therein; lysing a portion of red blood cells in said control sample; sizing said leukocytes in said control sample thereby generating a size distribution of said leukocytes in said control sample; mixing a substance, having a predetermined relationship with said malady, with said at least one test sample to form a mixture, and thereby allow at least a portion of said leukocytes present in said at least one test sample to react with said substance; lysing a portion of any red blood cells in said mixture; lysing a portion of any reacted leukocytes in said mixture; sizing said leukocytes in said mixture thereby generating a size distribution of said leukocytes in said mixture; and comparing said size distribution of said leukocytes in said mixture with said size distribution of said leukocytes in said control sample, and determine thereby if said malady is present in said subject.

Briefly stated, the invention is directed to a method for the diagnosis of a malady in a subject by the observing of a degree of reaction between the leukocytes in the subject's blood with a foreign entity having a predetermined relationship with the malady being diagnosed.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

My earlier Patent, identified above, described a test for use in the diagnosis of allergies by measuring the degree of reaction between the leukocytes in a subject's blood with a suspected allergen. The disclosure of that Patent is herein incorporated by reference.

What is not evident from a reading of that Patent, however, is my discovery that many common maladies, and some less common maladies, cause reactions in a subject's blood similar to those resulting from allergies. It is my theory that the reactions of the body's immune system in responding to the identification of an allergen, i.e. a leukocyte engulfing the allergen, enlarging and then extruding its contents, is basically identical to the bodily reactions to the introduction of other foreign entities recognized as being harmful, such as a virus or even a carcinogen. In sum, it is my theory that most maladies may be diagnosed by the observation of the reactions of the body's immune system, specifically, the size-distribution of the leukocytes in two samples of a subject's blood: a control sample which has no foreign entity added thereto, and a test sample which has at least one foreign entity added thereto.

The basic method and apparatus of the invention disclosed herein is contained in my earlier Patent, but the breadth of its applicability is significantly wider than heretofore realized, in its reach beyond merely diagnosing maladies other than allergies.

Figure 1:
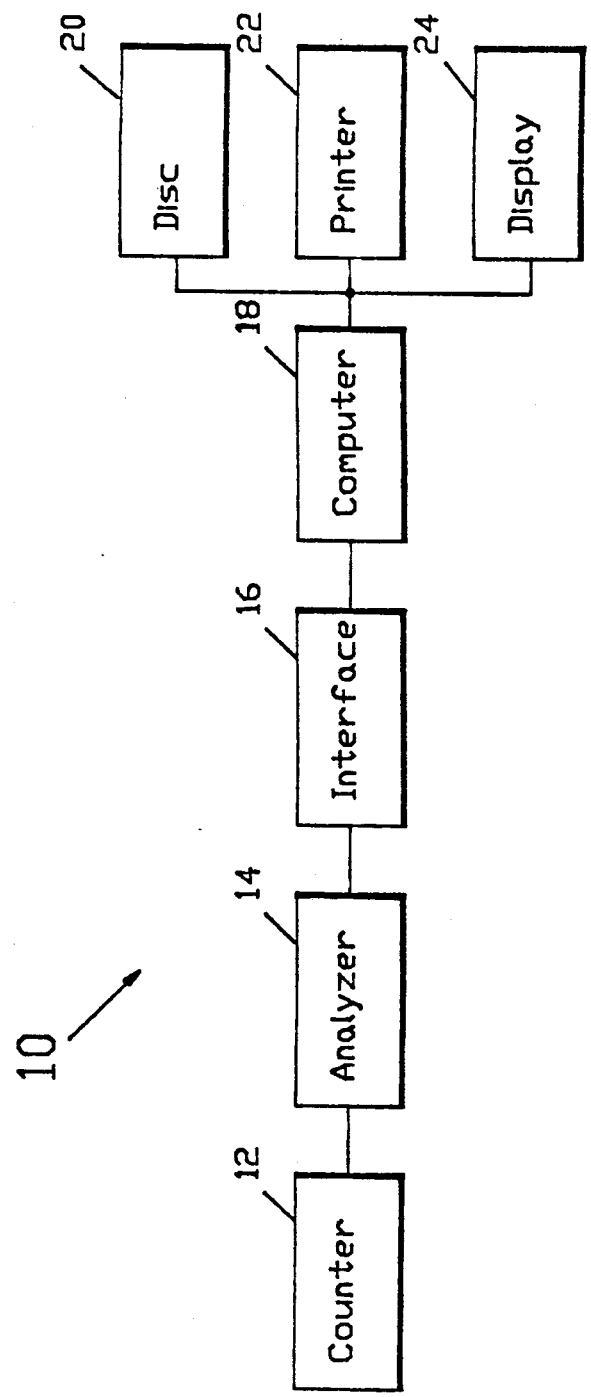
FIG. 1 is a block diagram showing the connection of the various components which make up the present inventive apparatus.

An apparatus in accordance with my invention, as shown generally at 10 in FIG. 1, comprises a counter 12, an analyzer 14, a computer interface 16 and a computer 18, each connected in series, and a disc 20, a printer 22 and a video display 24, each connected to the output of computer 18.

Figure 2:
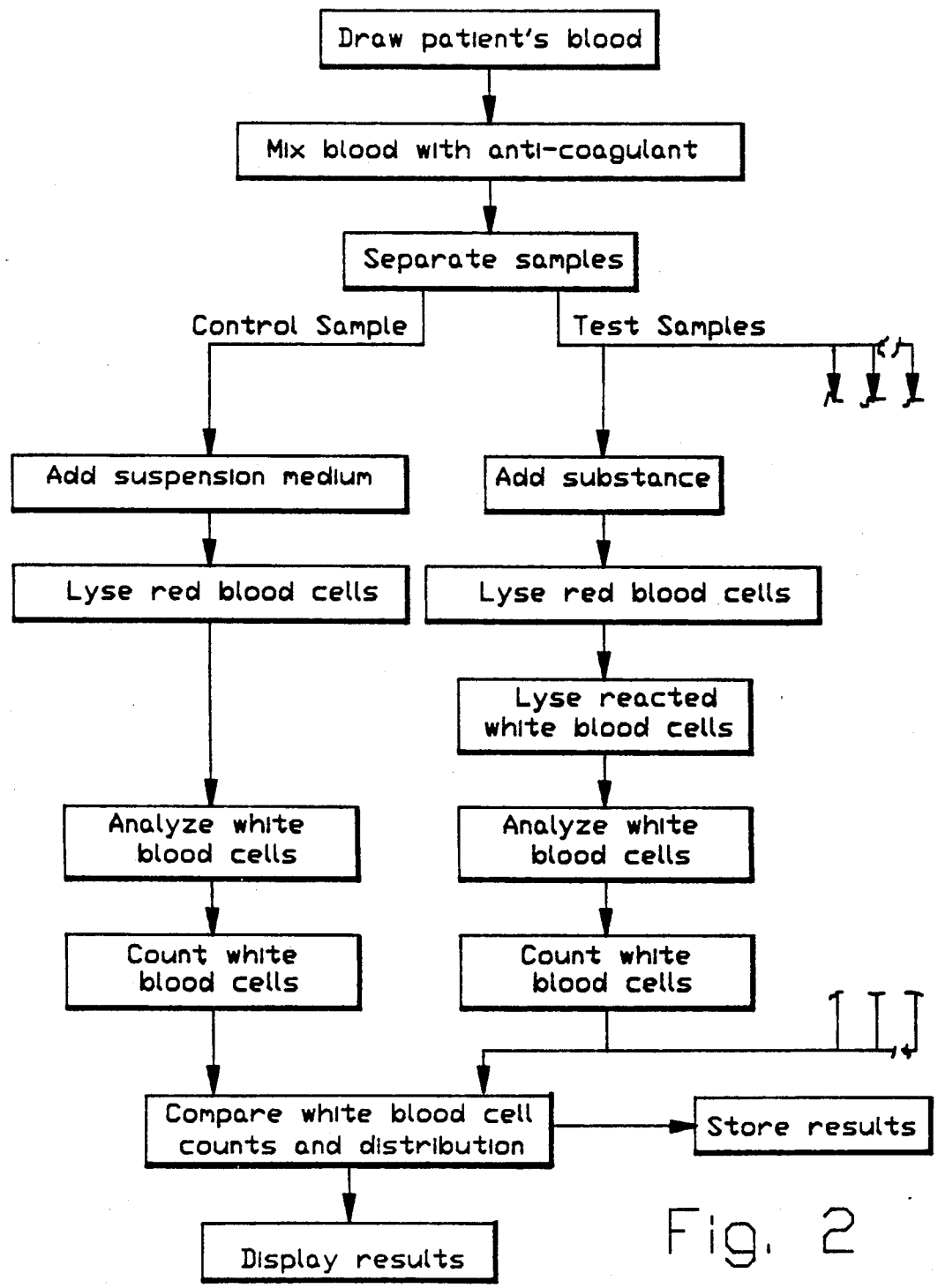
FIG. 2 is a flow chart showing the steps of the inventive method.

To commence the operation of the inventive apparatus (generally described in the flow chart of FIG. 2) a blood sample is first drawn from the person being tested (subject). Preferably, 10 cc of oxylated blood is drawn from the subject, using sodium citrate as an anti-coagulant (i.e. the blood is stored in blue top B-D brand vacutainers) to prevent clotting of the blood during the test. This single sample may be used to perform a wide variety of tests for a vast array of different maladies.

It is necessary to secure an even cellular distribution of leukocytes over the entire volume of the blood sample, and so it is necessary to transfer blood from the vacutainer to an apparatus (not shown) which will have the capability of continuous flow circulation, in known fashion. Such a device will cause the cells of the sample to be distributed generally evenly over the entire sample.

It is preferred that a single blood sample drawn from the subject be used during a battery of tests for a number of foreign entities, and so the blood drawn from the subject is separated into a plurality of smaller samples for testing. The preferred method of separation is to place 100 microliters of the drawn blood into a receptacle containing an appropriate suspension medium, e.g. either 1 or 2 ml of a balanced pH saline solution. The precise amount of the suspension medium used is not critical, except that the same amount thereof should be used throughout the test, i.e. in each sample of the same blood. This will ensure that measurements taken for the test and control samples may be directly compared by virtue of the fact that they both have a similar number of leukocytes and volume.

The ten cubic centimeters of drawn blood prepared as described will be suitable for approximately 75 tests.

After separation of the drawn sample into the control and test samples, the foreign entities are introduced into the test samples in the form of solutions.

Suitable solutions may be purchased commercially from any one of a number of suppliers. Alternatively, suitable solutions may be prepared by adding 100 mg of a dried extract of that foreign entity to 10 ml of Isoton II or III (distributed by Coulter), or any mixture thereof, or in 10 ml of a suitable diluting solution. In many instances, injectable paragen-free, sterilized water will be suitable, in others perhaps alchohol. The particluar diluting solution selected will depend upon the foreign entity being mixed, and the selection of an appropriate diluting solution is well within the knowledge of those of ordinary skill in the art. Once made, the mixture is allowed to stand for 24 hours at room temperature, and then filtered through a mesh capable of filtering solid particles.

Different solutions of foreign entities are introduced into the various test samples. It is preferred that one foreign entity be introduced into each test sample, but it is contemplated that, in some embodiments, each test sample may have a wide variety of foreign entities introduced thereto, so that a single drawn blood sample, which may otherwise be usable only for 75 tests, may be used over a much broader range of possible foreign entities. In such embodiments, a positive reaction (described below) for any group of foreign entities would require a subsequent test or tests to determine which of the multitude of foreign entities contained in that test sample was the specific foreign entity which caused the positive reaction. It is also preferred that an amount of the suspension medium, equal to that introduced to the test samples, be added to the control sample. This allows the direct comparison of the two samples, since they will have generally identical counts of leukocytes (before the studied reaction), and generally similar volumes.

At this point, each sample, i.e. the control sample and each test sample, will contain a mixture of suspension medium and whole blood, which in turn includes leukocytes, red blood cells and platelets. In addition, the test samples will have the solutions of foreign entities therein. The only cells which are of importance to the studied reaction, however, are the leukocytes, and so it is important that counter 12 only count those cells. In the preferred embodiment, counter 12 is Coulter Counter Model Z-M, which may be set to count the number of particles within a given size range. Thus, since platelets are much smaller than leukocytes, it is simple to avoid counting them by setting the minimum particle size at a size greater than that of platelets, and less than that of leukocytes, for example 4.8 microns.

To avoid counting red blood cells, which are of roughly comparable size to the leukocytes, it is preferred that those cells be eliminated. This is preferably accomplished by adding a substance which will immediately cause red blood cells to disintegrate (a "lysing" substance), for example a solution comprising one percent Saponin (Coulter) and the remainder bacteriostatic water. Alternatively, the red blood cells may be mechanically removed from the sample. After the red blood cells and reacted leukocytes are eliminated, preferably after a period of about 30 seconds, and counter 12 is set to the predetermined minimum size level, counter 12 may be used to count and size the leukocytes of the control sample. The results of the counting and sizing of the control sample are used as a reference for comparison of the results of the same counts performed on the control samples.

If the leukocytes in one or more of the test samples recognize any foreign entity as harmful, then they will react in the manner described, i.e. by getting larger, then breaking up and finally dissolving. These reactions will cause a distortion of the size distributions of the leukocytes in the positive test samples, since the number of leukocytes in lower volumetric size ranges will diminish, and the number of leukocytes in higher volumetric size ranges will increase, thereby producing a shift in the size-distributions of the counted leukocytes.

The output of counter 12 may be read visually, to determine if the number of white blood cells in the test sample is less than that of the control (indicating positive reaction) or it may be input to analyzer 14, such as the Coulter Channelyzer, to obtain cellular population distributions of the number of white blood cells present in each of a plurality of size-distribution ranges. This is referred to as "sizing".

The output of analyzer 14 may also be input to computer 18 through interface 16, in known fashion, to store the data and automatically compare the results of the count of each test sample to that of the control sample as well as the size-distribution of the white blood cells. If the number of white blood cells in a test sample is less than that of the control by more than the error factor of counter 12, then there is a positive reaction. The error factor of each piece of equipment used is readily available from its manufacturer, and may vary from manufacturer to manufacturer. In addition, if the comparison of the size-distribution results indicate enlargement of white blood cells, then there is also a positive reaction. Once all comparisons are made, the output of computer 18 may be displayed by any means desired, such as printer 22 or video display 24, and may also be stored on disc 20 for future reference.

Storing data is useful for later reference on the same subject at a later date. If a control sample of a subject's blood taken at a subsequent time is vastly different from that of a first test, then there may be an indication of a vast change in the state of that subject's immune system. This would suggest further testing to determine the cause of such a change.

It is here noted that the above description was made based on the assumption that a foreign entity is added to the test samples to produce thereby a reaction. This may not be effective in all instances. My theory is that, if the subject has been exposed to the foreign entity, the subject will have begun to produce antibodies specific thereto. The production of these antibodies in quantities sufficient to enable the use of this test takes place over about two days. If the subject has been exposed to the foreign entity more recently, the test may not be able to detect such exposure, due to an insufficient level of antibodies. Subsequent testing, of course, would reveal the exposure.

More seriously, however, the test will not work unless the subject has produced antibodies specific to the foreign entity. Not all individuals produce antibodies appropriate for all foreign entities. This is particularly true for carcinogens, for which no naturally occurring antibodies are present in the blood of most people.

The test will still work, however, with one modification. Instead of adding the foreign entity to the control sample, a different substance, such as an antibody, is introduced thereto. This modification will enable the diagnosis of a malady caused by the ingestion of a foreign entity by the subject, even if the subject does not produce the antibodies on his own. The addition of the antibodies to the test sample completes the requirement that all three components of the reaction: antibodies, foreign entity and leukocytes, be present in the test sample.

For example, with respect to the testing for a specific cancer, if the carcinogenic foreign entity is present in the subject's blood, the introduction of a monoclonal antibody specific to that carcinogenic foreign entity will enable the leukocytes in the subject's blood to attack the carcinogen, and the normally observed reaction will take place.

So long as an antibody is known for any specific foreign entity, the malady caused by the ingestion of that foreign entity may be diagnosed.

In this fashion, it may be objectively determined if the subject has a reaction to any of the tested foreign entities, and is therefore suffering from any of the tested maladies. Such a test may be used to test for any malady affecting the immune system, from influenza, to AIDS, to cancer. Any such malady may be tested for, and at a stage where treatment will be most effective, i.e. at as early a stage as possible.

It is also here noted that there is nothing in this description which will limit the application of this method to the human immune system. It is believed that this method is equally applicable, for example, in the field of veterinary medicine for any animal having an immune system.

As will be readily apparent to those skilled in the art, the above description represents the preferred, but nonetheless illustrative, embodiment of the invention, which may be realized in other specific forms without departing from its spirit or essential characteristics. For example, the entire apparatus may be automated so that once the sample of blood is drawn from the subject there need be no further human intervention or action until the results are complete. Therefore, the full scope of such invention is to be measured by the appended claims, giving thereto the full range of equivalence which comes within the meaning and range of the claims.

I claim:

1. A method for diagnosing the presence or absence of a malady affecting the immune system in a subject, said method comprising the steps of:
   counting a number of leukocytes in a first blood sample drawn from said subject;
   mixing a substance having a predetermined relationship with said malady with a second blood sample drawn from said subject to form a mixture, and thereby allow leukocytes of said second blood sample to react with said substance;
   counting a number of unreacted and reacted leukocytes in said mixture; and
   comparing said number of said leukocytes counted in said first blood sample with said number of unreacted and reacted leukocytes counted in said mixture, to determine if said leukocytes in said second blood sample reacted with said substance, thereby diagnosing the presence or absence of said malady in said subject.

2. The method of claim 1, wherein said counting a number of leukocytes of at least one of said first blood sample and said mixture is performed by counting a number of leukocytes within each of a plurality of varying size-distribution ranges.

3. The method of claim 2, further comprising the step of:
   producing a graph showing said number of leukocytes counted in each of said plurality of size-distribution ranges.

4. The method of claim 1, further comprising the step of:
   lysing a portion of any red blood cells present in said mixture prior to counting said number of unreacted and reacted leukocytes therein.

5. The method of claim 1, further comprising the step of:
   lysing a portion of said reacted leukocytes in said mixture prior to counting said number of unreacted and reacted leukocytes therein.

6. The method of claim 1, further comprising the step of:
   lysing a portion of any red blood cells present in said first blood sample prior to counting said number of leukocytes therein.

7. A method for diagnosing the presence or absence of a malady affecting the immune system in a subject having blood, said method comprising the steps of:
   separating a sample of said blood of said subject into a control sample and at least one test sample, each of said control sample and said at least one test sample having approximately equal distributions of leukocytes therein;
   lysing a portion of any red blood cells in said control sample;
   counting a number of leukocytes in said control sample;
   mixing a substance having a predetermined relationship with said malady with said at least one test sample to form a mixture, and thereby allow said leukocytes present in said at least one test sample to react with said substance, and form reacted leukocytes in said mixture if said subject suffers from said malady;
   lysing a portion of any red blood cells in said mixture;
   lysing a portion of said reacted leukocytes in said mixture;
   counting a number of unreacted and reacted leukocytes in said mixture;
   comparing said number of unreacted and reacted leukocytes in said mixture with said number of leukocytes in said control sample, to determine if at least a portion of said leukocytes in said test sample reacted with said substance, thereby indicating the presence or absence of said malady in said subject.

8. The method of claim 7, wherein at least one of said counting of said number of leukocytes in said control sample and said counting of said number of unreacted and reacted leukocytes in said mixture are performed by counting a number of leukocytes within each of a plurality of varying size-distribution ranges therein, and
   generating a size-distribution graph showing a size-distribution of leukocytes in each of said control sample and said mixture;
   comparing said size-distribution graph showing said size-distribution of said leukocytes in said control sample with said size-distribution graph showing said size-distribution of leukocytes in said mixture;
   whereby the presence of said malady in said subject is indicated by a significant difference therebetween.

9. The method of claim 7, wherein the determination of whether said substance has caused a reaction with said sample of a patient's blood is positive when said number of unreacted leukocytes counted in said mixture is less than said number of leukocytes counted by equipment in said control sample by an amount greater than an error factor of said equipment.

10. A method for diagnosing the presence or absence of a malady affecting the immune system in a subject, said method comprising the steps of:
    sizing a number of leukocytes in a first blood sample drawn from said subject;
    mixing a substance having a predetermined relationship with said malady with a second blood sample drawn from said subject to form a mixture, and thereby allow leukocytes present in said second blood sample to react with said second blood sample;
    sizing a number of unreacted and reacted leukocytes in said mixture; and
    comparing said sized leukocytes of said first blood sample with said sized unreacted and reacted leukocyte of said mixture, to determine thereby if at least a portion of said leukocytes in said second blood sample reacted with said substance, whereby the presence of said malady in said subject is indicated by a significant difference therebetween.

11. The method of claim 10, further comprising the step of:
    lysing a portion of any red blood cells present in said first blood sample prior to sizing said leukocytes therein.

12. The method of claim 10, further comprising the step of:
    lysing a portion of any red blood cells present in said second blood sample prior to sizing said unreacted and reacted leukocytes therein.

13. The method of claim 10, further comprising the step of:

lysing a portion of said reacted leukocytes in said mixture prior to sizing said unreacted and reacted leukocytes therein.

14. The method of claim 10, wherein at least one of said sizing of said leukocytes in said first blood sample and said sizing of said unreacted leukocytes in said mixture is performed by counting a number of leukocytes within each of a plurality of varying size-distribution ranges.

15. A method for diagnosing the presence or absence of a malady affecting the immune system in a subject, said method comprising the steps of:

separating a blood sample drawn from said subject into a control sample and at least one test sample, each of said control sample and said at least one test sample having approximately equal distributions of leukocytes therein;

lysing a portion of red blood cells in said control sample;

sizing said leukocytes in said control sample thereby generating a size distribution of said leukocytes in said control sample;

mixing a substance, having a predetermined relationship with said malady, with said at least one test sample to form a mixture, and thereby allow at least a portion of said leukocytes present in said at least one test sample to react with said substance;

lysing a portion of any red blood cells in said mixture;

lysing a portion of any reacted leukocytes in said mixture;

sizing said leukocytes in said mixture thereby generating a size distribution of said leukocytes in said mixture; and comparing said size distribution of said leukocytes in said mixture with said size distribution of said leukocytes in said control sample, and determine thereby if said malady is present in said subject.

16. The method of claim 15, wherein at least one of said sizing of said leukocytes in said control sample and said sizing of said leukocytes in said mixture is performed by counting a number of leukocytes within each of a plurality of varying size-distribution ranges, and generating a size-distribution of the counts of each of said control sample and said mixture; and comparing said size-distribution of said leukocytes in said control sample with said size-distribution of said leukocytes in said mixture, to determine thereby if said malady is present in said subject.

17. The method of claim 15, wherein the determination of whether said malady is present in said subject is positive when said size-distribution of said leukocytes in said mixture differs from said size-distribution of said leukocytes in said control sample to a degree greater than an established error factor.

18. The method of claim 15, wherein said substance is a foreign entity.

19. The method of claim 15, wherein said substance is an antibody.

* * * * *